(12) United States Patent
Ito et al.

(10) Patent No.: US 8,889,805 B2
(45) Date of Patent: *Nov. 18, 2014

(54) CARBOXYLATE METAL COMPLEX AND CATALYST FOR OLEFIN POLYMERIZATION

(75) Inventors: Shingo Ito, Tokyo (JP); Kyoko Nozaki, Tokyo (JP); Yoshikuni Okumura, Oita (JP); Junichi Kuroda, Oita (JP)

(73) Assignees: Showa Denko K.K., Tokyo (JP); The University of Tokyo, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/819,053
(22) PCT Filed: Jul. 22, 2011
(86) PCT No.: PCT/JP2011/066663
§ 371 (c)(1),
(2), (4) Date: Feb. 26, 2013
(87) PCT Pub. No.: WO2012/029432
PCT Pub. Date: Mar. 8, 2012

(65) Prior Publication Data
US 2013/0158223 A1  Jun. 20, 2013

(30) Foreign Application Priority Data
Aug. 31, 2010 (JP) .................. 2010-194143

(51) Int. Cl.
*C08F 4/80* (2006.01)
(52) U.S. Cl.
USPC ............. 526/172; 526/169.1; 526/318.6; 526/348; 526/352; 556/136
(58) Field of Classification Search
USPC ........ 526/172, 161, 330, 348, 169.1; 556/136
See application file for complete search history.

(56) References Cited

FOREIGN PATENT DOCUMENTS

JP  2007-046032 A  * 2/2007 ............ C08F 4/80
JP  2011-68881 A  4/2011
WO  2010-058849 A1  5/2010

OTHER PUBLICATIONS

Nakamura et al. J. Am. Chem. Soc. 2008, 130, 8128-8129.*

(Continued)

*Primary Examiner* — Rip A. Lee
(74) *Attorney, Agent, or Firm* — Sughrue Mion, PLLC (57) ABSTRACT

The present invention provides a metal complex of group 10 elements of the periodic table having a carboxylate structure represented by formula (C2); a catalyst for polymerization of olefin mainly comprising the metal complex; and a method for producing polymers by homopolymerizing olefin represented by formula (1), polymerizing two or more kinds of the above olefin, or copolymerizing olefin represented by formula (1) with polar group-containing olefin represented by formula (2) (the meaning of the symbols are as set forth in the description) using the catalyst. A metal complex of group 10 elements of the periodic table, in which all of the coordinating atoms to the metal are a hetero atom is stable and useful as a catalyst component for olefin polymerization, and can be used for a long time in homopolymerization of olefin or copolymerization of two or more kinds of olefin.

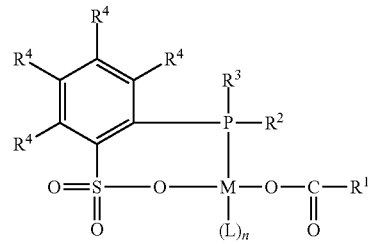

(C2)

$CH_2 = CHR^5$ (1)

$CH_2 = CR^6R^7$ (2)

11 Claims, 1 Drawing Sheet

(56) References Cited

OTHER PUBLICATIONS

Okanazawa et al. 90th Spring Meeting of Japan Chemical Society, 2010, Lecture Proceedings II, Mar. 12, 2010, p. 150, lecture No. 1 B2-B36.*

JP 2007-046032 A (Feb. 22, 2007); abstract and translation in English.*

International Search Report issued in PCT/JP2011/066663 dated Sep. 20, 2011.

Kanazawa, et al., "Sakusan Allyl to Ethylene no Haii Kyojugo," 90th Annual Meeting of Chemical Society of Japan, Spring (2010) Koen Yokoshu II, Mar. 12, 2010, Lecture No. 1 B2-36, p. 150.

Ito, et al., "Coordination—Insertion Copolymerization of Allyl Monomers with Ethylene," Journal of the American Chemical Society, Jan. 4, 2011, pp. 1232-1235, Scheme 2, vol. 133, No. 5.

Williams, et al., "Reactions of Vinyl Acetate and Vinyl Trifluoroacetate with Cationic Diimine Pd(II) and Ni(II) Alkyl Complexes: Identification of Problems Connected with Copolymerizations of These Monomers with Ethylene," Journal of American Chemical Society, 2005, pp. 5132-5146, vol. 127, No. 14.

Drent, et al., "Palladium catalysed copolymerisation of ethene with alkylacrylates: polar comonomer built into the linea polymer chain," Chem. Commun., 2002, pp. 744-745.

Ito, et al., "Copolymerization of Vinyl Acetate with Ethylene by Palladium/Alkylphosphine—Sulfornate Catalysts," Journal of American Chemical Society, 2009, pp. 14606-14607, vol. 131, No. 41.

* cited by examiner

CARBOXYLATE METAL COMPLEX AND CATALYST FOR OLEFIN POLYMERIZATION

CROSS REFERENCE TO RELATED APPLICATIONS

This is a National Stage of International Application No. PCT/JP2011/066663 filed Jul. 22, 2011, claiming priority based on Japanese Patent Application No. 2010-194143 filed Aug. 31, 2010, the contents of all of which are incorporated herein by reference in their entirety.

TECHNICAL FIELD

The present invention relates to a novel metal complex of group 10 elements of the periodic table, a catalyst mainly comprising the metal complex for olefin polymerization, and a method for producing a polymer using the catalyst.

BACKGROUND ART

In recent years, a method for producing a polymer using complexes of late transition metals as a catalyst for olefin polymerization has become known.

Generally, metal complexes having a metal-hydrogen bond or metal-carbon bond have been used as a catalyst system used for coordination polymerization.

J. Am. Chem. Soc., 127, 5132 (2005) (Non-patent document 1) discloses a polymerization mechanism and a catalyst deactivation mechanism in polymerization of vinyl acetate using a metal complex of group 10 elements of the periodic table. Particularly, the document proposes β-acetoxy elimination after the vinyl acetate insertion into the metal-alkyl bond as one of the catalyst deactivation mechanisms. This shows that the metal-acetoxy complex generated by β-acetoxy elimination does not have polymerization activity and it was generally considered that the olefin insertion into the metal-oxygen bond cannot happen.

Chem. Commun., 744 (2002) (Non-patent document 2) discloses copolymerization of ethylene and methyl acrylate using the product obtained by allowing the zero-valent late transition metal and ligand to react in advance as a catalyst. In this catalyst system, it is presumed that the generation of a metal-hydride complex initiates the polymerization reaction. However, it is considered that the decomposition of the catalyst species proceeds due to the low thermal stability of the metal-hydride complex, resulting in the low polymerization activity.

J. Am. Chem. Soc., 131, 14606 (2009) (Non-patent document 3) discloses the copolymerization of ethylene and vinyl acetate using the isolated metal-methyl complex catalyst, and shows that the polymerization activity was noticeably improved in the case of using the isolated metal-methyl complex catalyst compared to the case of using a metal-hydride complex as generated in situ. However, metal-alkyl complexes generally have a problem in the stability such that they tend to decompose by the impurities during the polymerization and there was a challenge for the industrial use.

PRIOR ART

Non-Patent Documents

Non-patent Document 1: J. Am. Chem. Soc., 127, 5132 (2005)
Non-patent Document 2: Chem. Commun., 744 (2002)
Non-patent Document 3: J. Am. Chem. Soc., 131, 14606 (2009)

DISCLOSURE OF THE INVENTION

Problems to Be Solved by the Invention

An object of the present invention is to provide a metal complex of group 10 elements of the periodic table which is more stable than conventional late transition metal catalysts for olefin polymerization, a catalyst mainly comprising the metal complex for olefin polymerization, and a method for producing a polymer using the catalyst. In the present specification, "olefin" means a hydrocarbon compound having an ethylenic carbon-carbon double bond with or without a polar group.

Means to Solve the Problem

As a result of intensive studies to solve the above-mentioned problems, the present inventors have developed a stable metal complex of group 10 elements of the periodic table, in which all of the coordinating atoms to the metal are a hetero atom, unlike the conventional late transition metal catalysts for olefin polymerization; have found that the olefin polymerization proceeds when the metal complex is used as a catalyst and accomplished the present invention.

That is, the present invention relates to the following [1] to [11].

[1] A carboxylate metal complex represented by formula (C1)

(C1)

(in the formula, M represents a metal atom of group 10 element in the periodic table; X represents a phosphorous atom (P) or an arsenic atom (As); $R^1$ represents a hydrogen atom or hydrocarbon group having 1 to 30 carbon atoms which may be substituted by one or more functional groups selected from a halogen atom, alkoxy group, aryloxy group, acyloxy group and amino group; $R^2$ and $R^3$ independently represent a hydrogen atom, alkoxy group, aryloxy group, acyloxy group, silyl group, amino group or hydrocarbon group having 1 to 30 carbon atoms which may be substituted by one or more functional groups selected from a halogen atom, alkoxy group, aryloxy group, acyloxy group and amino group; $R^2$ and $R^3$ may bond to each other to form a ring structure; Y represents divalent hydrocarbon group having 1 to 70 carbon atoms which may be substituted by one or more functional groups selected from a halogen atom, alkoxy group, aryloxy group, acyloxy group and amino group; L represents a neutral electron-donating ligand and n is 0, ½, 1 or 2.

[2] The carboxylate metal complex as described in [1] above, wherein the carboxylate metal complex represented by formula (C1) is represented by formula (C2)

(C2)

(in the formula, four R⁴s independently represent a hydrogen atom, alkyl group having 1 to 8 carbon atoms, alkoxy group having 1 to 8 carbon atoms, aryloxy group having 6 to 18 carbon atoms or a halogen atom; and M, $R^1$, $R^2$, $R^3$, L and n have the same meanings as in [1] above).

[3] The carboxylate metal complex as described in [2] above, wherein M in formula (C2) is Ni or Pd.

[4] The carboxylate metal complex as described in [2] or [3] above, wherein $R^1$ in formula (C2) is hydrocarbon group having 1 to 30 carbon atoms which may be substituted by a halogen atom.

[5] The carboxylate metal complex as described in [4] above, wherein $R^1$ in formula (C2) is methyl group or trifluoromethyl group.

[6] The carboxylate metal complex as described in [5] above, wherein $R^1$ in formula (C2) is methyl group.

[7] The carboxylate metal complex as described in any one of [2] to [6] above, wherein both of $R^2$ and $R^3$ in formula (C2) are isopropyl group or cyclohexyl group.

[8] The carboxylate metal complex as described in any one of [2] to [7] above, wherein all of $R^4$s in formula (C2) are a hydrogen atom.

[9] The carboxylate metal complex as described in any one of [2] to [8] above, wherein L in formula (C2) is 2,6-dimethylpyridine and n is 1.

[10] A catalyst for olefin polymerization mainly comprising the carboxylate metal complex described in any one of [1] to [9] above.

[11] A method for producing a polymer characterized in polymerizing olefin represented by formula (1) singly or in combination of two or more kinds thereof, or copolymerizing olefin represented by formula (1) and polar group-containing olefin represented by formula (2)

$$CH_2=CHR^5 \tag{1}$$

(In the formula, $R^5$ represents a hydrogen atom or hydrocarbon group having 1 to 20 carbon atoms)

$$CH_2=CR^6R^7 \tag{2}$$

(In the formula, $R^6$ represents a hydrogen atom or methyl group, $R^7$ represents —COOR⁸, —CN, —OCOR⁸, —CH₂—OCOR⁸, —CH₂OH, —CH₂—N(R⁹)₂ or —CH₂-Hal (R⁸ represents a hydrogen atom or hydrocarbon group having 1 to 5 carbon atoms, $R^9$ represents a hydrogen atom, hydrocarbon group having 1 to 5 carbon atoms or aromatic substituent having 6 to 18 carbon atoms or alkoxycarbonyl group, and Hal represents a halogen atom).

Effects of the Invention

The novel metal complex of group 10 elements of the periodic table of the present invention, in which all of the coordinating atoms are a hetero atom, is stable and useful as a catalyst component for olefin polymerization, and can be used for olefin homopolymerization or copolymerization of two or more kinds of olefin for a long period of time.

MODE FOR CARRYING OUT THE INVENTION

Metal Complex
The metal complex of the present invention is represented by formula (C1).

(C1)

In the formula, M represents a metal atom of group 10 element in the periodic table; X represents a phosphorous atom (P) or an arsenic atom (As); $R^1$ represents a hydrogen atom or hydrocarbon group having 1 to 30 carbon atoms which may be substituted by one or more groups selected from a halogen atom, alkoxy group, aryloxy group, acyloxy group and amino group; $R^2$ and $R^3$ independently represent a hydrogen atom, alkoxy group, aryloxy group, acyloxy group, silyl group, amino group or hydrocarbon group having 1 to 30 carbon atoms which may be substituted by one or more groups selected from a halogen atom, alkoxy group, aryloxy group, acyloxy group and amino group; $R^2$ and $R^3$ may bond to each other to form a ring structure; Y represents divalent hydrocarbon group having 1 to 70 carbon atoms which may be substituted by one or more functional groups selected from a halogen atom, alkoxy group, aryloxy group, acyloxy group and amino group; L represents a neutral electron-donating ligand and n is 0, ½, 1 or 2.

In the present specification, "hydrocarbon" includes saturated and unsaturated aliphatic hydrocarbon, alicyclic hydrocarbon and aromatic hydrocarbon.

The structure of the complex represented by formula (C1) is described below.

M represents an element of group 10 in the periodic table. Examples of the element of group 10 in the periodic table include nickel (Ni), palladium (Pd) and platinum (Pt), Ni and Pd are preferable and Pd is more preferable.

Single electron of the high-electronegative oxygen atom of Y—S(=O)₂—O— moiety coordinates to metal atom M. Since the bonding electron between Y—S(=O)₂—O-M is transferred from M to Y—S(=O)₂—O—, Y—S(=O)₂—O— and M may be indicated formally as an anion state and a cation state, respectively.

$R^1$ represents a hydrogen atom or hydrocarbon group having 1 to 30 carbon atoms which may be substituted by one or more groups selected from a halogen atom, alkoxy group, aryloxy group, acyloxy group and amino group. Examples of the hydrocarbon group having 1 to 30 carbon atoms which may be substituted by one or more groups selected from a halogen atom, alkoxy group, aryloxy group, acyloxy group and amino group include alkyl group, aryl group and cycloalkyl group. A preferred halogen atom in the hydrocarbon group having 1 to 30 carbon atoms which may be substituted by one or more groups selected from a halogen atom, alkoxy group, aryloxy group, acyloxy group and amino group is fluorine. Preferred alkoxy group is the one having 1 to 10 carbon atoms, including methoxy group, ethoxy group, propoxy group and isopropoxy group. Preferred aryloxy group is the one having 6 to 24 carbon atoms, including phenoxy group. Preferred acyloxy group is the one having 1 to 10 carbon atoms, including acetoxy group and pivaloxy group. Preferred amino group is the one having 1 to 10 carbon atoms, including dimethylamino group, diethylamino group and diisopropylamino group. As $R^1$, methyl group, trifluoromethyl group and phenyl group are more preferable due to the easy availability and from a cost point of view.

L represents a neutral electron-donating ligand. Neutral electron-donating ligand L is a compound which contains an electron-donating group and is capable of stabilizing a metal complex by coordinating to metal atom M as a two-electron ligand to thereby isolate a metal complex.

Examples of the neutral electron-donating ligand include those containing a sulfur atom such as dimethyl sulfoxide (DMSO). Examples of those containing a nitrogen atom include trialkyl amine having 1 to 10 carbon atoms, dialkyl amine, pyridine, 2,6-dimethylpyridine, quinoline, 2-methylquinoline, aniline, 2,6-dimethylaniline, 2,6-diisopropylaniline, N,N,N',N'-tetramethylethylenediamine (TMEDA), 4-(N,N-dimethylamino)pyridine (DMAP), acetonitrile and benzonitrile. Examples of those containing a phosphorous atom include trimethylphosphine, triisopropylphosphine, tributylphosphine, tri(t-butyl)phosphine, triphenylphosphine, tris(o-tolyl)phosphine and trifurylphosphine. Examples of those containing an oxygen atom include diethyl ether, tetrahydrofuran, 1,4-dioxane and 1,2-dimethoxyethane. From the viewpoint of a synthesis method, electron-donating ligands containing a nitrogen atom and those containing a phosphorous atom are preferable, and those containing a nitrogen atom are particularly preferable.

n represents the coordination number of the neutral electron-donating ligand L to metal atom M and is 0, ½, 1 or 2. n of ½ means that one bivalent electron-donating ligand coordinates to two metal complexes. n is preferably ½ or 1 to stabilize a metal complex. n of 0 means that there is no ligand.

X represents a phosphorous atom (P) or an arsenic atom (As), wherein two electrons coordinate to M. P is preferred as X for reasons of availability and the catalyst cost.

$R^2$ and $R^3$ independently represent a hydrogen atom, alkoxy group, aryloxy group, acyloxy group, silyl group, amino group, or a hydrocarbon group having 1 to 30 carbon atoms which may be substituted by one or more groups selected from a halogen atom, alkoxy group, aryloxy group, acyloxy group and amino group. Preferred alkoxy group is the one having 1 to 20 carbon atoms, including methoxy group, ethoxy group, propoxy group and isopropoxy group. Preferred aryloxy group is the one having 6 to 24 carbon atoms, including phenoxy group. Examples of silyl group includes trimethylsilyl group and examples of amino group include amino group, methylamino group and dimethylamino group. $R^2$ and $R^3$ may be the same or different from each other. $R^2$ and $R^3$ may bond to each other to form a ring structure. Examples of the hydrocarbon group having 1 to 30 carbon atoms represented by $R^2$ and $R^3$ which may be substituted by one or more groups selected from a halogen atom, alkoxy group, aryloxy group, acyloxy group and amino group include alkyl group, aryl group, cycloalkyl group and furyl group. Specific examples of the halogen atom, alkoxy group, aryloxy group, acyloxy group and amino group in the hydrocarbon group having 1 to 30 carbon atoms which may be substituted by one or more groups selected from a halogen atom, alkoxy group, aryloxy group, acyloxy group and amino group include the same as those in the explanation of $R^1$. As $R^2$ and $R^3$, alkyl group, cycloalkyl group and aryl group are preferable, and isopropyl group and cyclohexyl group are most preferable.

Examples of [$(R^2)(R^3)P$] moiety when X is P (a phosphorous atom) include the following structures. In the following structure formulae, the bonds between P and M or Y are not shown. In the structure formula, "Me" represents methyl group, "iPr" represents isopropyl group, and "tBu" represents t-butyl group.

[Chem. 6]

[Chem. 7]

Examples of [(R²)(R³)As] moiety when X is As (an arsenic atom) include the following structures. In the following structure formulae, the bonds between As and M or Y are not shown.

[Chem. 11]

Y represents a bivalent hydrocarbon group having 1 to 70 carbon atoms (crosslinked structure) which may be substituted by one or more functional groups selected from a halogen atom, alkoxy group, aryloxy group, acyloxy group and amino group. Examples of the bivalent hydrocarbon group having 1 to 70 carbon atoms which may be substituted by one or more functional groups selected from a halogen atom, alkoxy group, aryloxy group, acyloxy group and amino group include alkylene group and arylene group. Arylene group is particularly preferable.

The cross-linked structure Y is the crosslinking moiety which binds X and a sulfur atom (S). Specific examples of the cross-linked structure Y in which X is represented by a P atom are shown below. Here, multiple $R^{10}$s may be the same or different to each other and represent a hydrogen atom, halogen atom, hydrocarbon group having 1 to 20 carbon atoms, or a hydrocarbon group having 1 to 20 carbon atoms substituted by a halogen atom.

Substituents $R^2$ and $R^3$ may bond to Y moiety to form a ring structure. Specific examples include the structures as follows:

[Chem. 13]

Among the metal complexes represented by formula (C1), those represented by the following formula (C2) are particularly preferable.

[Chem. 14]

(C2)

In the formula, four $R^4$s independently represent a hydrogen atom, alkyl group having 1 to 8 carbon atoms, alkoxy group having 1 to 8 carbon atoms, aryloxy group having 6 to 18 carbon atoms or halogen atom; and M, $R^1$, $R^2$, $R^3$, L and n have the same meanings as those in formula (C1). Examples of the alkyl group having 1 to 8 carbon atoms include methyl group, ethyl group, propyl group and octyl group. Examples of the alkoxy group having 1 to 8 carbon atoms include methoxy group, ethoxy group, propoxy group and isopropoxy group. Examples of the aryloxy group having 6 to 18 carbon atoms include phenoxy group. Examples of the halogen atom include chlorine and fluorine.

In formula (C2), preferred $R^1$ is a methyl group. Both of $R^2$ and $R^3$ are preferably a cyclohexyl group or isopropyl group. Each of the four $R^4$s is preferably a hydrogen atom. L is preferably dimethyl sulfoxide, pyridine, 2,6-dimethylpyridine (lutidine), quinoline, 2-methylquinoline or N,N,N',N'-tetramethylethylenediamine, and 2,6-dimethylpyridine (lutidine) is particularly preferable. n is preferably ½ or 1, and 1 is particularly preferable. M is preferably Ni or Pd, and Pd is particularly preferable.

There is no particular limitation on the method for synthesizing metal complexes (C1) and (C2) of the present invention and the complexes can be synthesized according to a known method or a combination thereof. That is, the complexes can be synthesized by reacting zerovalent or bivalent M source, a ligand in formula (C1) or (C2) and a neutral electron-donating ligand L.

Examples of zerovalent M source include tris(dibenzylidene acetone)dipalladium and tetrakis(triphenylphosphine)palladium as a palladium source and tetracarbonyl nickel, bis(1,5-cyclooctadiene)nickel and tetrakis(triphenylphosphine)nickel as a nickel source.

Examples of bivalent M source include (1,5-cyclooctadiene)palladium chloride, (1,5-cyclooctadiene)(methyl)palladium chloride, (allyl)palladium chloride, palladium chloride, palladium bromide, palladium acetate, palladium nitrate, bis(acetonitrile)dichloropalladium, bis(benzonitrile)dichloropalladium, (N,N,N',N'-tetramethylethylenediamine)dichloro palladium(II), (N,N,N',N'-tetramethylethylenediamine)dimethyl palladium(II), bis(acetylacetonato)palladium(II), palladium(II) trifluoromethanesulfonate as a palladium source; and (allyl)nickel chloride, (allyl)nickel bromide, nickel chloride, nickel acetate, bis(acetylacetonato)nickel(II), (1,2-dimethoxyethane)dichloronickel(II), (1,2-dimethoxyethane) dibromonickel(II) and nickel(II) trifluoromethanesulfonate as a nickel source.

Metal complexes represented by formula (C1) and formula (C2) can also be synthesized by reacting an M-hydride complex or an M-alkyl complex (the two are collectively referred to as "(C3)") corresponding to the metal complex with allyl ester (2-1).

(C3)

(C1)

In the formula, $R^{11}$ represents a hydrogen atom or alkyl group having 1 to 6 carbon atoms, and $R^1$, $R^2$, $R^3$, X, Y, M, L and n have the same meanings as described above. While the above formula indicates the method for synthesizing metal complex (C1), metal complex (C2) can be synthesized in the same way.

The metal complexes represented by formula (C1) and formula (C2) can also be synthesized by reacting an M-halogen complex (C4) corresponding to the metal complex with carboxylate metal salt (2-2).

(C4)

(C1)

In the formula, $R^{12}$ represents a halogen atom, M' represents a metal atom, and $R^1$, $R^2$, $R^3$, X, Y, M, L and n have the same meanings as described above. While the above formula indicates the method for synthesizing metal complex (C1), metal complex (C2) can be synthesized in the same way.

Examples of the halogen atom represented by $R^{12}$ include a chlorine atom, a bromine atom or an iodine atom, and a chlorine atom or a bromine atom is preferable from a cost point of view.

Specific examples of carboxylate metal salts (2-2) which can be used in the synthesis method of the present invention include silver acetate, silver trifluoroacetate, silver propionate, silver 2-ethylhexanoate, lithium acetate, lithium trifluoroacetate, lithium propionate, lithium 2-ethylhexanoate, sodium acetate, sodium trifluoroacetate, sodium propionate, sodium 2-ethylhexanoate, potassium acetate, potassium trifluoroacetate, potassium propionate and potassium 2-ethylhexanoate.

The metal complex represented by formula (C1) or (C2) may be supported on a support to be used for polymerization. In this case, there are no particular limitations on the support and examples include an inorganic support such as silica gel and alumina and an organic support such as polystyrene, polyethylene and polypropylene. Examples of the method for depositing a metal complex on a support include a physical adsorption method of impregnating the support with a solution of the metal complex and drying it and a method of depositing the metal complex onto a support by chemically bonding the metal complex to a support.

[Monomer]

Olefin, which is the first monomer used in the method for producing the polymer of the present invention, is represented by formula (1).

[Chem. 17]

$$CH_2=CHR^5 \quad (1)$$

In formula (1), $R^5$ represents a hydrogen atom or hydrocarbon group having 1 to 20 carbon atoms and is preferably a hydrogen atom, alkyl group having 1 to 3 carbon atoms or aryl group having 6 to 20 carbon atoms. Specifically, examples of olefin of formula (1) include ethylene, propylene, 1-butene, 1-hexene, 4-methyl-1-pentene, 1-octene and styrene. Among these, ethylene and propylene are particularly preferable. One of these compounds may be used independently or two or more of them may be used in combination.

A polar group-containing olefin, which is the second monomer used for polymerization in the present invention, is represented by formula (2).

[Chem. 18]

$$CH_2=CR^6R^7 \quad (2)$$

In formula (2), $R^6$ represents a hydrogen atom or methyl group. $R^7$ represents —$COOR^8$, —CN, —$OCOR^8$, —$CH_2$—$OCOR^8$, —$CH_2OH$, —$CH_2$—$N(R^9)_2$ or —$CH_2$-Hal ($R^8$ represents a hydrogen atom, hydrocarbon group having 1 to 5 carbon atoms; $R^9$ represents a hydrogen atom, hydrocarbon group having 1 to 5 carbon atoms, aromatic substituent having 6 to 18 carbon atoms or alkoxycarbonyl group; and Hal represents a halogen atom). $R^8$ is preferably a hydrogen atom or alkyl group having 1 to 3 carbon atoms, and methyl group is particularly preferable. $R^9$ is preferably a hydrogen atom, alkyl group having 1 to 3 carbon atoms, phenyl group, benzyl group, t-butoxycarbonyl group or benzyloxycarbonyl group. The halogen atom of Hal is preferably a chlorine atom or a bromine atom.

Specific examples of the polar group-containing vinyl compound represented by formula (2) include vinyl acetate, allyl acetate, allyl alcohol, methyl methacrylate, methacrylic acid, methyl acrylate, acrylic acid, acrylonitrile, allyl amine, N-allylaniline, N-t-butoxycarbonyl-N-allylamine, N-benzyloxycarbonyl-N-allylamine, N-benzyl-N-allylamine, allyl chloride and allyl bromide. Among these, vinyl acetate, allyl acetate, methyl methacrylate, methyl acrylate and acrylonitrile are particularly preferable. One of these compounds may be used independently or two or more of them may be used in combination.

Examples of the combination of olefin represented by formula (1) and the polar group-containing olefin represented by formula (2) include ethylene and vinyl acetate, ethylene and allyl acetate, ethylene and ally alcohol, ethylene and methyl methacrylate, ethylene and methacrylic acid, ethylene and methyl acrylate, ethylene and acrylic acid, ethylene and acrylonitrile, ethylene and allylamine, ethylene and N-allylaniline, ethylene and N-t-butoxycarbonyl-N-allylamine, ethylene and N-benzyloxycarbonyl-N-allylamine, ethylene and N-benzyl-N-allylamine, ethylene and allyl chloride, ethylene and allyl bromide, propylene and vinyl acetate, propylene and allyl acetate, propylene and allyl alcohol, propylene and methyl methacrylate, propylene and methyl acrylate, propylene and acrylic acid, propylene and acrylonitrile, propylene and allylamine, propylene and N-allylaniline, propylene and N-t-butoxycarbonyl-N-allylamine, propylene and N-benzyloxycarbonyl-N-allylamine, propylene and N-benzyl-N-allylamine, propylene and allyl chloride and propylene and allyl bromide. Among these, preferred are ethylene and vinyl acetate, ethylene and allyl acetate, ethylene and allyl alcohol, ethylene and methyl methacrylate, ethylene and methyl acrylate, ethylene and acrylonitrile, ethylene and allyl chloride, and ethylene and allylamine from the viewpoint of the polymer performance and economic efficiency.

In the method for producing the (co)polymer of the present invention, in addition to the monomers represented by formulae (1) and (2), one or more kinds of a third monomer may be incorporated to be copolymerized.

The third monomers include ethyl vinyl ether, propyl vinyl ether, norbornene and carbon monoxide.

[Polymerization Method]

There are no particular limitations on the method of polymerizing monomers and the monomers can be polymerized by a widely-used method. That is, a process such as a solution polymerization method, a suspension polymerization method and a gas-phase polymerization method is available. Particularly preferred are a solution polymerization method and a suspension polymerization method. The polymerization mode may employ either of a batch mode and a continuous mode. Also, either of a single stage polymerization or a multistage polymerization can be employed.

The molar ratio between the metal complex catalyst represented by formula (C1) or (C2) and the total amount of monomers (monomers/metal complex) is within the range of from 1 to 10,000,000, preferably the range of from 10 to 1,000,000, more preferably the range of from 100 to 100,000.

The blending ratio of the monomers represented by formulae (1) and (2) is to be appropriately adjusted depending on the composition ratio of the targeted copolymer. This includes a case where a third monomer is used.

There are no particular limitations on the polymerization temperature. The polymerization is generally conducted at a temperature in the range of from −30 to 200° C., preferably in the range of from 0 to 180° C., more preferably in the range of from 20 to 150° C.

The polymerization is conducted at a polymerization pressure, wherein the internal pressure consists mostly of the pressure of olefin represented by formula (1), in the range from normal pressure to 20 MPa, preferably in the range from normal pressure to 10 MPa.

The polymerization time can be appropriately adjusted depending on the processing mode and the polymerization activity of the catalyst, and can be as short as several minutes or as long as several thousand hours.

It is preferable to fill the atmosphere in the polymerization system with an inert gas such as nitrogen and argon to prevent components other than monomers to be polymerized such as air, oxygen and moisture being mixed into the atmosphere to retain the catalyst activity. In the case of the solution polymerization, an inert solvent may be used in addition to monomers to be polymerized. There are no particular limitations on the inert solvent, and examples include aliphatic hydrocarbon such as pentane, hexane and heptane; alicyclic hydrocarbon such as cyclopentane, cyclohexane and cycloheptane; aromatic hydrocarbon such as benzene, toluene and xylene; halogenated aliphatic hydrocarbon such as chloroform, methylene chloride, carbon tetrachloride, dichloroethane and tetrachloroethane; halogenated aromatic hydrocarbon such as chlorobenzene, dichlorobenzene and trichlorobenzene; aliphatic ester such as methyl acetate and ethyl acetate; and aromatic ester such as methyl benzoate and ethyl benzoate.

After completion of the polymerization reaction, the (co)polymer as a reaction product is to be isolated by post-treatment using a known operation and treating method (e.g. neutralization, extraction with solvents, washing with water, liquid separation, distillation with solvents and reprecipitation).

The (co)polymer can be molded into the form of a pellet, film, sheet and the like under conditions for general thermoplastic resin.

The obtained (co)polymer can be a product per se by molding such as injection molding, extrusion and film processing. Or the (co)polymer may be added to polyolefin and the like to be used as a modifier of the surface features such as adhesiveness and printing performance; a compatibility agent between nonpolar polyolefin and highly-polar other resins; and a dispersing agent of pigments and the like. The copolymer may also be used for purposes such as paint, ink, adhesive agent, binder, plasticizer, lubricant, lubricant oil and surface active agent.

EXAMPLES

Hereinafter, the present invention is described in greater detail by referring to Examples and Comparative Examples. The present invention is by no means limited thereto.

[Method for Analyzing a Metal Complex Compound]

The structures of Metal complex 1 and Metal complex 2 obtained in the examples were determined by X-ray crystal structure analysis using an single crystal X-ray diffractometer (Mercury CCD) manufactured by Rigaku Corporation. Mo-Kα radiation (Λ=0.71069 Å) was used as X-ray source, and radiation within the range of $2\theta \leq 50°$ was used. Diffraction intensity was corrected using Lorentz factor. The structure was elucidated by the direct method via SIR-97, and optimized using SHELXL-97. The atoms other than hydrogen were anisotropically optimized and the hydrogen atoms were arranged using the AFIX instruction.

[Method for Analyzing the Polymer Structure]

The structure of the copolymers obtained in Examples was determined by various analysis of the NMR spectra using JNM-ECS400 manufactured by JEOL Ltd. The content of the monomer unit derived from the polar group-containing olefin represented by formula (2) and the terminal structure of the copolymer were determined by analyzing $^{13}$C-NMR spectrum (90° pulse at 9.0 microseconds, spectrum width: 31 kHz, relaxation time: 10 seconds, acquisition time: 10 seconds, times of accumulating FID signals: 5,000 to 10,000 times) through the inverse-gated decoupling method at 120° C. using 1,2,4-trichlorobenzene (0.55 ml) as a solvent and Cr(acac)$_3$ (10 mg) as relaxation agent.

A number average molecular weight and a weight average molecular weight were calculated by size extrusion chromatography in which polystyrene is employed as a standard substance using a high-temperature GPC apparatus, HLC-8121GPC/HT, manufactured by Tosoh Corporation, provided with TSKgel GMHHR-H(S) HT column (two columns of 7.8 mm I.D.×30 cm arranged in series) manufactured by Tosoh Corporation (solvent: 1,2-dichlorobenzene, temperature: 145° C.).

Metal Complex 1c:

Metal complex 1c was synthesized according to the following reaction scheme:

[Chem. 19]

1a: R' = cyclohexyl

1b: R' = cyclohexyl

1c: R' = cyclohexyl (a) Synthesis of Compound 1a n-Butyllithium (manufactured by Kanto Chemical Co., Inc., 1.65 M hexane solution, 5.1 ml, 8.4 mmol) was added to a tetrahydrofuran (THF) solution (20 ml) of benzenesulfonic acid (manufactured by Tokyo Chemical Industry Co., Ltd., 0.66 g, 4.2 mmol) at 0° C. under argon atmosphere and the mixture was stirred for 2.5 hours at room temperature. After cooling the reaction container to −78° C., chlorodicyclohexylphosphine (manufactured by Sigma-Aldrich, 0.89 mg, 3.8 mmol) was added thereto at −78° C. and stirred for 24 hours at room temperature. After ceasing the reaction with trifluoroacetic acid (manufactured by Tokyo Chemical Industry Co., Ltd., 0.50 M THF solution, 8.4 ml, 4.2 mmol), the precipitate formed was collected by filtration and dried under reduced pressure to obtain 2-(dicyclohexylphosphino)benzenesulfonic acid (compound 1a). The yield was 0.66 g (85%).

$^1$H-NMR (400 MHz, CDCl$_3$): δ 0.98-0.27 (m, 4H), 1.30-1.58 (m, 6H), 1.62-1.78 (m, 4H), 1.88 (br s, 4H), 2.28 (br s, 2H), 3.33 (br s, 2H), 5.19 (br d, $^1J_{PH}$=370 Hz, 1H), 7.48-7.58 (m, 2H), 7.80 (br s, 1H), 8.27 (br s, 1H);

$^{13}$C-NMR (101 MHz, CDCl$_3$): δ 25.0 (s), 25.6-26.2 (m), 28.8 (br), 30.3 (br), 34.6 (br d, $^1J_{PC}$=40 Hz), 113.4 (br d, $^1J_{PC}$=87 Hz), 128.8 (d, $J_{PC}$=9 Hz), 130.1 (d, $J_{PC}$=9 Hz), 135.4 (br), 137.1 (br), 150.5 (br);

$^{31}$P-NMR (162 MHz, CDCl$_3$): δ 52.8 (d, $^1J_{PH}$=370 Hz) (90%), 20.8 (d, $^1J_{PH}$=530 Hz) (10%);

Anal. calcd for C$_{18}$H$_{27}$O$_3$PS, C, 60.99; H, 7.68.
found: C, 60.90; H, 7.55.

(b) Synthesis of Metal Complex 1b

A methylene chloride solution (6 ml) of (COD)PdMeCl (synthesized according to "Inor. Chem., 1993, 32, 5769-5778; COD: 1,5-cyclooctadiene; 0.32 g; 1.2 mmol) was added to a methylene chloride solution (16 ml) of 2-(dicyclohexylphosphino)benzenesulfonic acid; compound 1a) (0.43 g, 1.2 mmol) and diisopropylethylamine (manufactured by Wako Chemical Pure Chemical Industries Ltd.; 1.1 ml, 6.0 mmol) under argon atmosphere and the mixture was stirred for one hour at room temperature. After condensing the solvent, the precipitation was removed by filtration and the filtrate was added to hexane. The precipitate formed was collected by filtration, washed with hexane and then dried under reduced pressure to obtain metal complex 1b. The yield was 0.66 g (85%).

$^1$H-NMR (500 MHz, CDCl$_3$): δ 0.71 (d, $^3J_{PH}$=1.4 Hz, 3H, PdCH$_3$), 1.11-1.35 (m, 8H), 1.45 (d, J=6.6 Hz, 6H, HNCH(CH$_3$)$_2$), 1.57 (d, J=6.6 Hz, 6H, HNCH(CH$_3$)$_2$), 1.57 (t, J=7.3 Hz, 3H, HNCH$_2$CH$_3$), 1.60-1.70 (m, 6H), 1.72-1.84 (m, 4H), 2.12-2.28 (m, 4H), 3.29 (dq, J=7.3, 5.0 Hz, 2H, HNCH$_2$CH$_3$), 3.92-4.01 (m, 2H, HNCH(CH$_3$)$_2$), 7.45 (dd, J=7.2, 7.2 Hz, 1H), 7.49 (dd, J=7.6, 7.6 Hz, 1H), 7.59 (dd, J=7.3, 7.3 Hz, 1H), 8.21 (ddd, J=7.7, 3.6, 1.3 Hz, 1H), 8.87 (br, 1H, NH);

$^{13}$C-NMR (101 MHz, CDCl$_3$): δ −7.3 (s, PdCH$_3$), 12.0 (s, HNCH$_2$CH$_3$), 17.9 (s, HNCH(CH$_3$)$_2$), 19.2 (s, HNCH(CH$_3$)$_2$), 26.0 (s), 26.9-27.4 (m), 28.7 (s), 29.4 (d, $J_{PC}$=4 Hz), 35.6 (d, $^1J_{PC}$=25 Hz), 42.4 (s, HNCH$_2$CH$_3$), 54.6 (s, HNCH(CH$_3$)$_2$), 125.5 (d, $^1J_{PC}$=33 Hz), 128.3 (d, $J_{PC}$=7 Hz), 128.9 (d, $J_{PC}$=6 Hz), 130.3 (s), 132.5 (s), 150.9 (d, $^2J_{PC}$=11 Hz);

$^{31}$P-NMR (162 MHz, CDCl$_3$): δ 31.7;

Anal. calcd for C$_{27}$H$_{49}$ClNO$_3$PPdS, C, 50.62; H, 7.71; N, 2.19.
found: C, 50.49; H, 8.00, N, 2.12.

(c) Synthesis of Metal Complex 1c

A methylene chloride solution (4 ml) of metal complex 1b (0.19 g, 0.30 mmol) was added to a methylene chloride suspension (2 ml) of potassium carbonate (0.42 g, 3.0 mmol) and 2,6-lutidine (manufactured by Tokyo Chemical Industry Co., Ltd., 0.33 g, 3.1 mmol) under argon atmosphere and stirred for one hour at room temperature. Solid remained after distilling away the solvent under reduced pressure was washed with diethyl ether and extracted with methylene chloride. The extract was filtered through by Celite (dry diatom earth) and slowly added to hexane (40 ml). The precipitate formed was collected by filtration, washed with hexane and then dried under reduced pressure to obtain metal complex 1c. The yield was 0.12 g (70%).

$^1$H-NMR (400 MHz, CDCl$_3$): δ 0.32 (d, $^3J_{PH}$=2.3 Hz, 3H, PdCH$_3$), 1.12-1.47 (m, 8H), 1.60-1.94 (m, 10H), 2.22-2.33 (m, 4H), 3.18 (s, 6H, CH$_3$ of lutidine), 7.12 (d, J=7.7 Hz, 2H), 7.47 (dd, J=7.6, 7.6 Hz, 1H), 7.52 (dddd, J=7.6, 7.6, 1.4, 1.4 Hz, 1H), 7.58 (dd, J=8.1, 8.1 Hz, 1H), 7.60 (dd, J=7.5, 7.5 Hz, 1H), 8.29 (ddd, 7.8, 3.9, 1.5 Hz, 1H);

$^{13}$C-NMR (101 MHz, CDCl$_3$): δ −9.4 (d, $^2J_{PC}$=4.8 Hz, PdCH$_3$), 26.3 (s, CH$_3$ of lutidine), 26.9-27.5 (m), 28.6 (s), 29.6 (d, $J_{PC}$=3 Hz), 35.5 (d, $^1J_{PC}$=26 Hz), 122.5 (s), 122.5 (s), 124.6 (d, $^1J_{PC}$=35 Hz), 128.9 (d, $J_{PC}$=7 Hz), 129.0 (d, $J_{PC}$=6 Hz), 130.7 (s), 132.4 (s), 138.1 (s). 151.0 (d, $^2J_{PC}$=12 Hz), 159.0 (s); $^{31}$P-NMR (162 MHz, CDCl$_3$): δ 27.5;

Anal. calcd for C$_{26}$H$_{38}$NO$_3$PPdS, C, 53.65; H, 6.58; N, 2.51. found: C, 53.51; H, 6.74; N, 2.40.

Synthesis of Metal Complex 2c

Metal complex 2c was synthesized according to the following reaction scheme:

[Chem. 20]

2a: R' = isopropyl

2b: R' = isopropyl

2c: R' = isopropyl (a) Synthesis of Compound 2a 2-(Diisopropylphosphino)benzenesulfonic acid (Compound 2a) was obtained in the same way as in the above-mentioned synthesis of Compound 1a except that chlorodiisopropylphosphine (manufactured by Sigma-Aldrich, 19.0 g, 125 mmol) was used instead of chlorodicyclohexylphosphine. The yield was 26.8 g (78%).

$^1$H-NMR (400 MHz, CDCl$_3$): δ1.25 (dd, J=21.6, 7.0 Hz, 6H), 1.53 (dd, J=21.8, 7.2 Hz, 6H), 3.45 (m, 2H), 5.42 (br d, $^1J_{PH}$=380 Hz), 7.58 (tdd, J=7.6, 2.8, 1.1 Hz, 1H), 7.69 (ddd, J=15.1, 7.7, 0.7 Hz, 1H), 7.83 (dd, J=7.6, 7.6 Hz, 1H), 8.27 (dd, J=7.5, 4.4 Hz, 1H);

$^{13}$C-NMR (101 MHz, CDCl$_3$): δ19.4 (s), 24.5-27.7 (m), 114.4 (br d, J=93 Hz), 129.1 (d, J=8.6 Hz), 130.3 (d, J=12.5 Hz), 134.7-137.1 (m), 150.7 (br s);

$^{31}$P-NMR (162 MHz, CDCl$_3$): δ62.5 (d, $^1J_{PH}$=380 Hz) (83%), 31.0 (d, $^1J_{PH}$=460 Hz) (17%)

(b) Synthesis of Metal Complex 2b

Metal complex 2b was obtained in the same way as in the above-mentioned synthesis of Metal complex 1b except that Compound 2a (2-(diisopropylphosphino)benzenesulfonic acid, 16.3 g, 59.3 mmol) was used instead of Compound 1a. The yield was 33.7 g (99%).

$^1$H-NMR (500 MHz, CDCl$_3$): δ0.73 (d, J=1.8 Hz, 3H), 1.20-1.29 (m, 12H), 1.45-1.59 (m, 15H), 2.54 (dt, J=21.9, 7.0 Hz, 2H), 3.29 (d, J=7.1 Hz, 2H), 3.97 (t, J=6.9 Hz, 2H), 7.43-7.52 (m, 2H), 7.57 (t, J=7.0 Hz, 1H), 8.22-8.24 (m, 1H);

$^{13}$C-NMR (101 MHz, CDCl$_3$): δ−7.79 (s), 12.16 (s), 17.91 (s), 18.54 (s), 19.21-19.28 (m), 25.93 (d, J=25.9 Hz), 42.58 (s), 54.69 (s), 125.25 (s), 125.58 (s), 128.8 (d, J=6.7 Hz), 129.13 (d, J=5.8 Hz), 130.58 (s), 132.48 (s), 150.89 (d, J=10.5 Hz);

$^{31}$P-NMR (162 MHz, CDCl$_3$): δ38.4 (s)

(c) Synthesis of Metal Complex 2c

Metal complex 2c was obtained in the same way as in the above-mentioned synthesis of Metal complex 1c except that Metal complex 2b (33.7 g, 58.5 mmol) was used instead of Metal complex 1b. The yield was 27.6 g (94%).

$^1$H-NMR (400 MHz, CDCl$_3$): δ0.34 (d, J=2.3 Hz, 3H), 1.32 (ddd, J=49.9, 16.0, 7.0 Hz, 12H), 2.58 (dt, J=22.3, 7.2 Hz, 2H), 3.18 (s, 6H), 7.12 (d, J=7.8 Hz, 2H), 7.46 (t, J=7.4 Hz, 1H), 7.53 (t, J=7.6 Hz, 1H), 7.58 (t, J=7.7 Hz, 2H), 8.29-8.32 (m, 1H);

$^{13}$C-NMR (101 MHz, CDCl$_3$): δ−10.10 (d, J=4.8 Hz), 18.44 (s), 19.29 (d, J=4.8 Hz), 25.91 (d, J=25.9 Hz), 26.20 (s), 122.72 (d, J=3.8 Hz), 124.56 (d, J=35.5 Hz), 129.19 (t, J=6.7 Hz), 131.03 (d, J=1.9 Hz), 132.39 (s), 138.30 (s), 151.13 (d, J=10.5 Hz), 159.17 (s);

$^{31}$P-NMR (162 MHz, CDCl$_3$): δ34.4 (s);

Anal. Calcd for C$_{20}$H$_{30}$NO$_3$PPdS, C, 47.86; H, 6.02; N, 2.79. Found: C, 47.92; H, 5.98; N, 2.51.

Example 1

Synthesis of Metal Complex 1

[Chem. 21]

Cy = cyclohexyl

Figure 1:
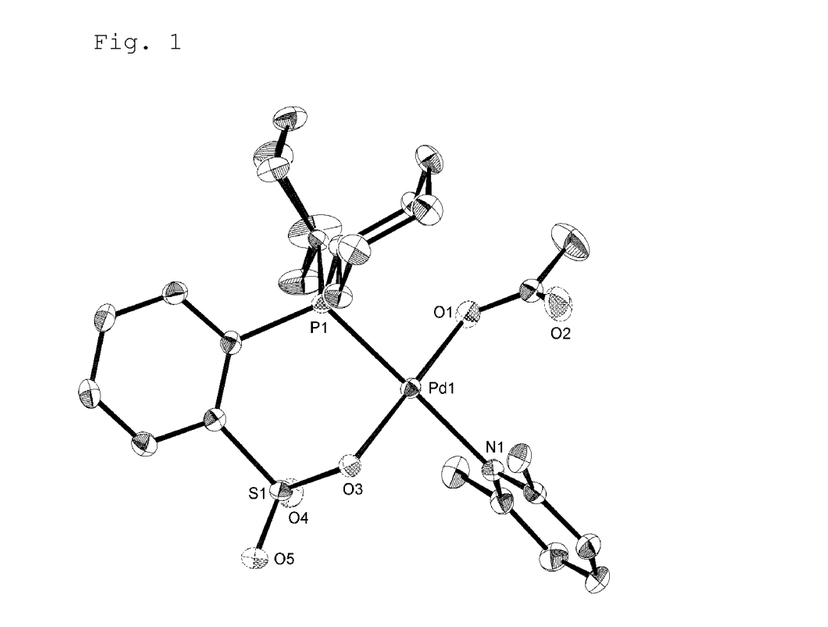
FIG. 1 shows an X-ray structure analysis of metal complex 1 prepared in Example 1.

The toluene (10 ml)/allyl acetate (10 ml) suspension of Metal complex 1c (0.12 g, 0.20 mmol) was heated to 80° C. and stirred for one hour under nitrogen atmosphere. After concentrating the reaction solution, methylene chloride (10 ml) was added to the residue and the participate was removed by filtration using a syringe filter. Hexane (15 ml) was slowly added to the filtration to perform recrystallization. The precipitated crystals were recovered by filtration, washed with hexane, and then dried under reduced pressure to obtain Metal complex 1. The yield was 0.083 g (66%). Furthermore, single crystals of the obtained Metal complex 1 were produced from a methylene chloride/hexane solution to determine the structure by X-ray crystal structure analysis. The X-ray structure analysis of Metal complex 1 is shown in FIG. 1.

$^1$H-NMR (400 MHz, CDCl$_3$): δ 1.04-0.2.44 (m, 25H), 3.42 (s, 6H), 7.06, (d, J=7.6 Hz, 2H), 7.53-7.62 (m, 4H), 8.17 (m, 1H).

$^{13}$C-NMR (101 MHz, CDCl$_3$): δ 22.7 (s), 24.7 (s), 26.1 (s), 27.1-27.3 (m), 28.1 (d, $^1J_{pc}$=19 Hz), 34.7 (d, $^1J_{pc}$=25 Hz), 121.7 (s), 122.1 (s), 122.8 (d, $J_{pc}$=3 Hz), 128.7 (d, $J_{pc}$=7 Hz), 130.1 (d, $J_{pc}$=6 Hz), 131.9 (s), 132.1 (s), 138.7 (s), 148.9 (d, $J_{pc}$=10 Hz), 160.1 (s), 176.7 (s).

$^{31}$P-NMR (162 MHz, CDCl$_3$): δ 17.0 (s)

Example 2

Synthesis of Metal Complex 2

[Chem. 22]

Figure 2:
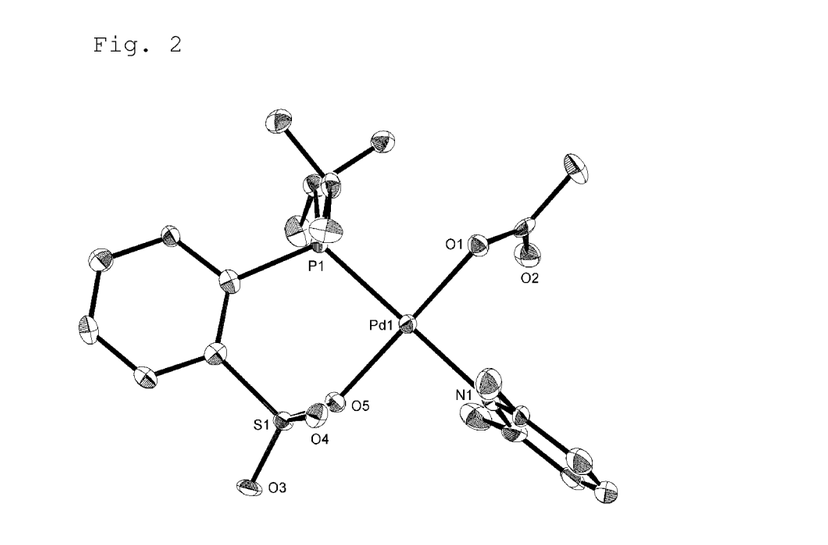
FIG. 2 shows an X-ray structure analysis of metal complex 2 prepared in Example 2.

Metal complex 2 was synthesized using Metal complex 2c in the same way as in Example 1. That is, toluen (94 ml)/allyl acetate (94 ml) suspension of Compound 2c (1.2 g, 2.4 mmol) was heated to 80° C. and stirred for two hours under nitrogen atmosphere. After concentrating the reaction solution, methylene chloride (10 ml) was added to the residue and the participate was removed by filtration using a syringe filter. Hexane (15 ml) was slowly added to the filtrate to perform recrystallization. The precipitated crystals were collected by filtration, washed with t-butyl methyl ether and hexane, and then dried under reduced pressure to obtain Metal complex 2. The yield was 1.1 g (83%). Furthermore, single crystals of the obtained Metal complex 2 were produced from acetone/hexane to determine the structure by X-ray crystal structure analysis. The X-ray structure analysis of Metal complex 2 is shown in FIG. 2.

$^1$H-NMR (400 MHz, CDCl$_3$): δ 1.36-1.52 (m, 12H), 1.75 (s, 3H), 2.51-2.60 (m, 2H), 3.42 (s, 6H), 7.06 (d, 2H, J=7.2 Hz), 7.55-7.64 (m, 4H), 8.20 (br, 1H);

$^{13}$C-NMR (101 MHz, CDCl$_3$): δ 17.7 (s), 17.8 (s), 22.5 (s), 24.5 (s, CH$_3$ of lutidine), 25.0 (d, $^1J_{PC}$=26.5 Hz), 121.4 (d, $^1J_{PC}$=39.8 Hz), 122.6 (s), 128.5 (d, $J_{PC}$=5.7 Hz), 129.8 (d, $J_{PC}$=5.8 Hz), 131.6 (s), 131.8 (s), 138.5 (s), 148.5 (d, $^2J_{PC}$=8.3 Hz), 159.8 (s), 176.7 (s)

Reference Example 1

Comparison of Stability of Metal Complex 2c and Metal Complex 2 in the Presence of Acetic Acid An experiment for comparing the stability of Metal complex 2c and Metal complex 2 in the presence of acetic acid was conducted. That is, a deuterated toluene solution of acetic acid (0.062 M, 0.6 ml, 0.037 mmol) was added to an NMR tube (inner diameter of 5 mm) filled with Metal complex 2c (0.0037 mmol) and Metal complex 2 (0.0037 mmol) respectively, for the $^1$H-NMR measurement. After heating the NMR tubes at 80° C. for ten hours, $^1$H-NMR was again measured. In addition to the peak derived from Metal complex 2c, the peak derived from Metal complex 2 (δ 1.74 ppm, 3.44 ppm, 8.22 ppm) and the peak derived from 2,6-dimethylpyridine (lutidine) (δ 2.38 ppm) decomposed and dissociated from the center metal were observed in the reaction solution containing Metal complex 2c. The abundance ratio of these was calculated to be 81.7% of Metal complex 2c, 10.6% of Metal complex 2 and 7.7% of dissociated lutidine by the integral value of lutidine. In contrast, a peak derived from a complex other than Metal complex 2 was not observed in the reaction solution containing Metal complex 2. The peak of acetic acid was observed at 1.59 ppm and at 9.80 ppm, which can be distinguished from the above-mentioned peaks of Metal complex 2, Metal complex 2c and lutidine.

Protonic acid such as acetic acid and acrylic acid exists as an impurity in the polar-group containing olefin, which is a monomer to be polymerized. The results of Reference Example 1 show that the metal complex of the present invention is remarkably stable against the impurity and difficult to be decomposed by the impurity even in the polymerization reaction.

Example 3

Ethylene Homopolymerization (Preparation of Polymer 1)

A toluene solution (75 ml) of metal complex catalyst 2 (0.50 mmol) was added into a 120 ml-volume autoclave under nitrogen atmosphere. After filling the autoclave with ethylene so that the inner pressure is 3.0 MPa, the content of the autoclave was stirred at 80° C. for 15 minutes. After cooling the autoclave to room temperature, the reaction solution was added to methanol (400 ml). The copolymer formed was collected by filtration, washed with methanol and dried under reduced pressure to obtain polymer 1. The yield was 0.24 g. The number average molecular weight and weight average molecular weight of the copolymer were 19,000 and 42,000, respectively, and Mw/Mn was 2.2.

Example 4

Copolymerization of Allyl Acetate and Ethylene (Preparation of Copolymer 2)

A toluene solution (37.5 ml) of metal complex catalyst 2 (0.10 mmol) was added into a 120 ml-volume autoclave containing allyl acetate (37.5 ml, 34.9 g, 350 mmol) under nitrogen atmosphere. After filling the autoclave with ethylene so that the inner pressure is 3.0 MPa, the content of the autoclave was stirred at 80° C. for five hours. After cooling the autoclave to room temperature, the reaction solution was added to methanol (400 ml). The copolymer formed was collected by filtration, washed with methanol and dried under reduced pressure to obtain Polymer 2. The yield was 2.7 g. The number average molecular weight and weight average molecular weight of the copolymer were 12,000 and 25,000, respectively, and Mw/Mn was 2.1. The allyl acetate content in Polymer 2 was determined to be 3.1% by molar fraction by $^{13}$C-NMR spectrum using the inverse-gated decoupling method.

Example 5

Copolymerization of Allyl Acetate and Ethylene (Preparation of Polymer 3)

A toluene solution (37.5 ml) of metal complex catalyst 2 (0.010 mmol) was added into a 120 ml-volume autoclave containing allyl acetate (37.5 ml, 34.9 g, 350 mmol) under nitrogen atmosphere. After filling the autoclave with ethylene so that the inner pressure is 3.0 MPa, the content of the autoclave was stirred at 80° C. for 25 hours. After cooling the autoclave to room temperature, the reaction solution was added to methanol (400 ml). The copolymer formed was collected by filtration, washed with methanol and dried under reduced pressure to obtain Polymer 3. The yield was 2.2 g. The number average molecular weight and weight average molecular weight of the copolymer were 12,000 and 28,000, respectively, and Mw/Mn was 2.3. The allyl acetate content in Polymer 3 was determined to be 3.4% by molar fraction by $^{13}$C-NMR spectrum using the inverse-gated decoupling method.

Comparative Example 1

Copolymerization of Allyl Acetate and Ethylene Using a Pd-Hydride Complex as a Catalyst Methylene chloride (3.75 ml) was added into a 50 ml-volume autoclave containing Compound 2b (0.12 mmol) and Pd2(DBA)3.CHCl3 (DBA: dibenzylideneacetone, 0.10 mmol) and stirred for ten minutes under argon atmosphere. It is presumed that a Pd-hydride complex is formed as a catalyst species (Reference document: J. Am. Chem. Soc., 131, 14605 (2009)). Subsequently, toluene (3.75 ml) and allyl acetate (7.5 ml, 70 g, 70 mmol) were added to the catalyst solution. After filling the autoclave with ethylene so that the inner pressure is 3.0 MPa, the content of the autoclave was stirred at 80° C. for 15 hours. After cooling the autoclave to room temperature, methanol (about 20 ml) was added into the autoclave. The copolymer formed was collected by filtration, washed with methanol and dried under reduced pressure to obtain a polymer. The yield was 1.7 g. The number average molecular weight and weight average molecular weight of the copolymer were 4,000 and 9,000, respectively, and Mw/Mn was 2.7. The allyl acetate content in the copolymer was determined to be 2.7% by molar fraction by $^{13}$C-NMR spectrum using the inverse-gated decoupling method.

Example 6

Copolymerization of Allyl Acetate and Ethylene (Preparation of Polymer 4)

A toluene solution (188 ml) of metal complex catalyst 2 (0.050 mmol) was added into a 500 ml-volume autoclave containing allyl acetate (188 ml, 174 g, 1740 mmol) under nitrogen atmosphere. After filling the autoclave with ethylene so that the inner pressure is 3.0 MPa, the content of the autoclave was stirred at 80° C. for 50 hours. After cooling the autoclave to room temperature, the reaction solution was added to methanol (1,000 ml). The copolymer formed was collected by filtration, washed with methanol and dried under reduced pressure to obtain Polymer 4. The yield was 23 g. The number average molecular weight and weight average molecular weight of the copolymer were 12,000 and 28,000, respectively, and Mw/Mn was 2.3. The allyl acetate content in Polymer 4 was determined to be 3.4% by molar fraction by $^{13}$C-NMR spectrum using the inverse-gated decoupling method.

Example 7

Synthesis of Metal Complex 3

[Chem. 23]

Cy = Cyclohexyl

Bis(1,5-cyclooctadiene)nickel (0.14 g, 0.50 mmol), 2-(dicyclohexylphosphino)benzenesulfonic acid (compound 1a, 0.21 g, 0.60 mmol), 2,6-dimethylpyridine (0.11 g, 1.0 mmol) and THF (30 ml) were stirred at room temperature for five hours under argon atmosphere. Allyl acetate (1 ml, 0.93 g, 9.3 mmol) was added to the reaction solution to allow the reaction to proceed further. After filtering the reaction solution, the filtrate was concentrated under reduced pressure to obtain 0.12 g (43%) of orange powder. It was confirmed by the $^{31}$P-NMR spectrum that the powder was Metal complex 3.

$^{31}$P-NMR (162 MHz, CD$_2$Cl$_2$): δ 16.6 (s)

Example 8

Ethylene Homopolymerization (Preparation of Polymer 5)

A toluene solution (6 ml) was added into a 50 ml-volume autoclave containing metal complex catalyst 3 (0.050 mmol) under nitrogen atmosphere. After filling the autoclave with ethylene so that the inner pressure is 3.0 MPa, the content of the autoclave was stirred at 80° C. for seven hours. After cooling the autoclave to room temperature, methanol (20 ml) was added into the autoclave. The polymer formed was collected by filtration, washed with methanol and dried under reduced pressure to obtain Polymer 5. The yield was 0.12 g. The number average molecular weight and weight average molecular weight of the polymer were 2,800 and 9,800, respectively, and Mw/Mn was 3.5.

The invention claimed is:

1. A carboxylate metal complex represented by formula (C1);

(in the formula, M represents a metal atom of group 10 element in the periodic table; X represents a phosphorous atom (P) or an arsenic atom (As); R$^1$ represents a hydrogen atom or hydrocarbon group having 1 to 30 carbon atoms which may be substituted by one or more functional groups selected from a halogen atom, alkoxy group, aryloxy group, acyloxy group or amino group; R$^2$ and R$^3$ independently represent a hydrogen atom, alkoxy group, aryloxy group, acyloxy group, silyl group, amino group or hydrocarbon group having 1 to 30 carbon atoms which may be substituted by one or more functional groups selected from a halogen atom, alkoxy group, aryloxy group, acyloxy group or amino group; R$^2$ and R$^3$ may bond to each other to form a ring structure; Y represents divalent hydrocarbon group having 1 to 70 carbon atoms which may be substituted by one or more functional groups selected from a halogen atom, alkoxy group, aryloxy group, acyloxy group or amino group; L represents a neutral electron-donating ligand and n is 0, ½, 1 or 2.

2. The carboxylate metal complex as claimed in claim 1, wherein the carboxylate metal complex represented by formula (C1) is represented by formula (C2);

(C2)

(in the formula, four $R^4$s independently represent a hydrogen atom, alkyl group having 1 to 8 carbon atoms, alkoxy group having 1 to 8 carbon atoms, aryloxy group having 6 to 18 carbon atoms or a halogen atom; and M, $R^1$, $R^2$, $R^3$, L and n have the same meanings as in claim 1.

3. The carboxylate metal complex as claimed in claim 2, wherein M in formula (C2) is Ni or Pd.

4. The carboxylate metal complex as claimed in claim 2, wherein $R^1$ in formula (C2) is hydrocarbon group having 1 to 30 carbon atoms which may be substituted by a halogen atom.

5. The carboxylate metal complex as claimed in claim 4, wherein $R^1$ in formula (C2) is methyl group or trifluoromethyl group.

6. The carboxylate metal complex as claimed in claim 5, wherein $R^1$ in formula (C2) is methyl group.

7. The carboxylate metal complex as claimed in claim 2, wherein both of $R^2$ and $R^3$ in formula (C2) are isopropyl group or cyclohexyl group.

8. The carboxylate metal complex as claimed in claim 2, wherein all of $R^4$s in formula (C2) are a hydrogen atom.

9. The carboxylate metal complex as claimed in claim 2, wherein L in formula (C2) is 2,6-dimethylpyridine and n is 1.

10. A catalyst for olefin polymerization mainly comprising the carboxylate metal complex claimed in claim 1.

11. A method for producing a polymer which comprises polymerizing an olefin represented by formula (1) singularly or in combination of two or more kinds thereof, or copolymerizing an olefin represented by formula (1) and polar group-containing olefin represented by formula (2);

$$CH_2=CHR^5 \quad (1)$$

in the formula, $R^5$ represents a hydrogen atom or hydrocarbon group having 1 to 20 carbon atoms;

$$CH_2=CR^6R^7 \quad (2)$$

in the formula, $R^6$ represents a hydrogen atom or methyl group, $R^7$ represents —$COOR^8$, —CN, —$OCOR^8$, —$CH_2$—$OCOR^8$, —$CH_2OH$, —$CH_2$—$N(R^9)_2$ or —$CH_2$-Hal, $R^8$ represents a hydrogen atom or hydrocarbon group having 1 to 5 carbon atoms, $R^9$ represents a hydrogen atom, hydrocarbon group having 1 to 5 carbon atoms or aromatic substituent having 6 to 18 carbon atoms or alkoxycarbonyl group, and Hal represents a halogen atom, wherein the polymerization reaction is carried out in the presence of a carboxylate metal complex represented by the formula (C1);

(C1)

in the formula, M represents a metal atom of group 10 element in the periodic table; X represents a phosphorous atom (P) or an arsenic atom (As); $R^1$ represents a hydrogen atom or hydrocarbon group having 1 to 30 carbon atoms which may be substituted by one or more functional groups selected from a halogen atom, alkoxy group, aryloxy group, acyloxy group or amino group; $R^2$ and $R^3$ independently represent a hydrogen atom, alkoxy group, aryloxy group, acyloxy group, silyl group, amino group or hydrocarbon group having 1 to 30 carbon atoms which may be substituted by one or more functional groups selected from a halogen atom, alkoxy group, aryloxy group, acyloxy group or amino group; $R^2$ and $R^3$ may bond to each other to form a ring structure; Y represents divalent hydrocarbon group having 1 to 70 carbon atoms which may be substituted by one or more functional groups selected from a halogen atom, alkoxy group, aryloxy group, acyloxy group or amino group; L represents a neutral electron-donating ligand and n is 0, ½, 1 or 2.

* * * * *